United States Patent [19]

Benziger et al.

[11] Patent Number: 5,401,707
[45] Date of Patent: Mar. 28, 1995

[54] VANADIUM/PHOSPHORUS OXIDE OXIDATION CATALYST

[75] Inventors: Jay B. Benziger, Lawrenceville; Vadim Guliants, Princeton; Sankaran Sundaresan, Mercerville, all of N.J.

[73] Assignee: The Trustees of Princeton University, Princeton, N.J.

[21] Appl. No.: 161,891

[22] Filed: Dec. 3, 1993

[51] Int. Cl.$^6$ ............................................... B01J 23/22
[52] U.S. Cl. ..................................... 502/209; 502/353; 502/200; 556/13; 556/14; 556/26; 549/259
[58] Field of Search ....................... 502/209, 353, 200; 556/13, 14, 26; 549/259

[56] References Cited

U.S. PATENT DOCUMENTS

| | | | |
|---|---|---|---|
| 3,864,280 | 2/1975 | Schneider | 502/209 |
| 4,454,061 | 6/1984 | Johnson | 252/625 |
| 5,137,860 | 8/1992 | Ebner et al. | 502/209 |
| 5,288,880 | 2/1994 | Matsuura | 502/209 |

*Primary Examiner*—Anthony Mc Farlane
*Attorney, Agent, or Firm*—Mathews, Woodbridge & Collins

[57] ABSTRACT

A vanadium/phosphorus oxide oxidation catalyst suitable for catalytic oxidation of $C_4$ feed stock in the preparation of maleic anhydride is formed by calcining an intercalation complex of the formula $VOHPO_4 \cdot 0.5\text{-}H_2O \cdot (\{C_nH_{2n+}\{-X\})_z$ in which n has a value of from 0 to 20, z has a value of from about 1.5 to about 1.9; and X is an oxygen- or nitrogen-containing functional group operable to form hydrogen bonds with the structural P—OH and water groups of the complex.

10 Claims, No Drawings

VANADIUM/PHOSPHORUS OXIDE OXIDATION CATALYST

This invention was made with government support under grant number CTS-9100130, awarded by the National Science Foundation. The government has certain rights in this invention.

The present invention relates to an improved vanadium/phosphorus oxide oxidation catalyst.

BACKGROUND OF THE INVENTION

Maleic anhydride is staple article of commerce used in the production of polyesters. It is prepared, inter alia, through the catalytic oxidation of butane, available for example from petroleum refinery streams. See, e.g., U.S. Pat. No. 3,864,280. The catalyst of choice for this oxidation is one comprising vanadium, phosphorus, and oxygen, generally known as a vanadium/phosphorus oxide oxidation catalyst or phosphorus-vanadium mixed oxide catalyst.

It has been proposed that vanadyl (IV) pyrophosphate, $(VO)_2P_2O_7$, is the active phase in the selective oxidation of n-butane to maleic anhydride. The pyrolytic precursor to vanadyl (IV) pyrophosphate is believed to be vanadyl (IV) hydrogen phosphate hemihydrate, or $VOHPO_4 \cdot (H_2O)_{0.5}$. This material has long been recognized as a layered material, the —POH groups forming interlayer hydrogen bonds and the water molecule being shared by two vanadyl octahedra which are face-linked.

A variety of such catalysts and methods for their production have been described.

U.S. Pat. No. 3,864,280 describes a crystalline phosphorus-vanadium mixed oxide hydrocarbon oxidation catalyst in which the vanadium has an average valence of from +3.9 to +4.6, the P:V ratio is from 0.9:1 to 1.8:1, and the B-phase content is at least 25%.

U.S. Pat. No. 4,043,943 describes forming a phosphorus-vanadium-oxygen precursor by calcining an intermediate obtained by reacting a vanadium compound with phosphorus compound in an oxygen-containing solvent containing less than 20% water.

U.S. Pat. No. 4,100,106 describes a process in which a water precipitated salt complex formed from tetravalent vanadium salt and orthophosphoric acid is calcined at a temperature of at least 300° C.

U.S. Pat. No. 4,116,868 describes a catalyst prepared by calcining a phosphorus-vanadium-oxygen precursor formed in the presence of a small amount of surfactant.

U.S. Pat. No. 4,132,670 describes a crystalline phosphorus-vanadium mixed oxide hydrocarbon oxidation catalyst in which the vanadium has an average valence of from +4.0 to +4.5, the V:P ratio is about 1:1, and the intrinsic surface area is from 1 m²/g to 10 m²/g.

U.S. Pat. No. 4,288,372 describes a catalyst similar to that set forth in U.S. Pat. No. 3,864,280 but having a surface area greater than 10 m²/g and containing lanthanum as a promoter.

U.S. Pat. No. 4,337,174 describes forming a phosphorus-vanadium-oxygen precursor which, prior to calcining, is heated at 130° to 170° C. and dried.

U.S. Pat. No. 4,418,003 describes the formation of a phosphorus-vanadium oxide catalyst by reacting a vanadium compound with phosphorus pentoxide in an acidic alcoholic medium.

U.S. Pat. No. 4,769,477 describes an attrition-resistant phosphorus-vanadium oxide catalyst incorporating silicon dioxide.

Various other catalysts are specified in, for example, U.S. Pat. Nos. 4,062,873, 4,333,853, and 4,562,268.

DETAILED DESCRIPTION

The present invention pertains to an intercalated vanadium complex which upon being calcined forms a vanadium/phosphorus oxide oxidation catalyst of improved specificity. This complex is represented by the formula:

$$VOHPO_4 \cdot 0.5H_2O \cdot (\{C_nH_{2n+}\}-X)_z \qquad \text{I.}$$ 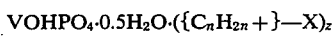

in which X is an oxygen- or nitrogen-containing functional group operable to form hydrogen bonds with the structural P—OH and water groups of the complex, n has a value of from 0 to 20 when X is a nitrogen-containing functional group or a value of from 1 to 20 when X is an oxygen-containing functional group; and z has a value of from about 1.5 to about 1.9.

The invention also relates to the vanadium/phosphorus oxide oxidation catalyst formed by calcining the intercalated vanadium complex of Formula I in the presence of a reducing agent and at a temperature of at least 400° C., and to the improvement in the catalytic oxidation of $C_4$ feed stock to form maleic anhydride by employing the vanadium/phosphorus oxide oxidation catalyst so obtained.

In Formula I, X can be any oxygen- or nitrogen-containing functional group operable to form hydrogen bonds with the structural P—OH and water groups of the complex as for example carboxyl, carbalkoxy, amido, amino, carbamoyl, etc. Preferably, X is a primary amino group.

X is bound to an alkyl group of from 1 to 20 carbon atoms, preferably 3 to 12 carbon atoms. Typical of such group are methyl, ethyl, n-propyl, n-butyl, n-pentyl, n-hexyl, n-octyl, n-dodecyl, n-tetradecyl, etc. Moreover when X is an amino group, n can be zero; i.e., an ammonia molecule.

The present complexes are prepared first by forming vanadyl (IV) hydrogen phosphate hemihydrate. This can be done according to known procedures, e.g., that of Milberger et al., U.S. Pat. No. 4,333,853. Intercalation of the vanadyl (IV) hydrogen phosphate hemihydrate then is performed by refluxing in a large molar excess of alkylamine until equilibrium is achieved. This can range from one to seven days, typically about two days. This procedure is suitable for compounds of Formula I in which n=3 to 6.

For complexes in which n=0 or 2, the desired complexes are readily obtained simply by allowing the derivative to stand in an atmosphere of ammonia, methylamine or ethylamine.

For complexes in which n>6, the desired complexes are readily obtained through exchange by refluxing a pentyl or hexyl derivative in an excess of a compound $C_nH_{2n+}$—X in which n is 7 or more. For compounds of the formula $C_nH_{2n+}$—X which are solid, a concentrated solution (as for example a 2M solution) in N,N-dimethylacetamide can be employed equally well. In each variation, the product can be isolated through simple filtration.

X-ray analysis indicates an increase in $D_{001}$ spacings of 2.19 Å per n. Since the increase for each carbon atom in a normal trans, trans alkylamine is estimated to be 1.27 Å, the amine bilayer appears to be tilted at 59.6°, corresponding to arcsin {2.19/2*1.27}.

Scanning electron microscopy demonstrates a change from typical rosette morphology of $VOHPO_4 \cdot 0.5H_2O$ to the sheet-like layered morphology of the complex. IR analysis indicates partial ionization, showing bands at 1625–1380 cm$^{-1}$ characteristic of ammonium cations, as well as at 3295–3250 cm$^{-1}$, corresponding to the characteristic bicuspid peak of the free amine.

While not wishing to be bound by any theory, it is believed the complexes involve intercalated $C_nH_{2n}$-layers closely packed on the VHP layer with interlayer spacing increasing with the value of n.

The complexes so obtained are calcined by heating the complex at 400° C. in the presence of a reducing agent. This can be done conveniently by using a $C_4$ feedstock, e.g., 2% butane in air. Hence the complex can be employed directly in the catalytic oxidation of butane, becoming effective after a short induction period during which it becomes calcined.

The following examples will serve to further typify the nature of the invention but should not be construed as a limitation on the scope thereof which is defined solely by the appended claims.

EXAMPLE 1

Preparation of Vanadyl (IV) Hydrogen Phosphate Hemihydrate

Sixteen grams of vanadium pentoxide are added with stirring to 140 mL of isobutanol. The mixture is heated at reflux for 16 hours and a solution of 20 g of 100% phosphoric acid in isobutanol is added. The reaction mixture is heated at reflux for 8 hours. The product is isolated by filtration and air dried at 150° C. for 2 hours.

EXAMPLE 2

Intercalation Procedure A

One gram of vanadyl (IV) hydrogen phosphate hemihydrate in a large molar excess of alkylamine (n-propylamine, n-butylamine, n-pentylamine, or n-hexylamine) is heated at reflux for approximately 72 hours or until equilibrium is achieved. The solid is collected by filtration and dried under helium at 373° K. for 2 hours.

Alternatively the same procedure can be employed using a 2M solution of the alkylamine in N,N-dimethylacetamide in place of neat alkylamine.

Packing densities of the indicated alkyl groups in the interlayer space $V_p$ given hereinafter are calculated from the ratio of the alkyl chain volume $V_c$ to the interlayer volume $V_t$ per unit area of layer surface; e.g., 1 cm$^2$:

$V_p = V_c/V_t$
$V_c = x \cdot N \cdot V_a$
$V_t = d_{001} - d°$ where x is the average number of amine molecules per acid site on the layer;

N is $5.61 \times 10^{14}$;

$V_a$ is the volume of the individual alkyl group; and $d°$ is the extrapolated value of $d_{001}$ for $n_c = 0$, corresponding to the combined height of the phosphate layer and $-NH_3+$ group.

The following are representative elemental analyses, thermogravimetric analyses, and packing densities:

n-propyl (n=3, z=1.63) Calc.: C, 21.88%; H, 6.22%; N 8.51%. Found: C, 21.88%; H, 6.08%; N 7.85%. X-ray analysis $D_{001}$ spacing = 14.70. Thermogravimetric analysis indicates z is about 1.60. The packing density ($V_p$) is 0.99.

n-butyl (n=4, z=1.64) Calc.: C, 26.98%; H, 6.87%; N 7.87%. Found: C, 26.54%; H, 6.85%; N 7.60%. X-ray analysis $D_{001}$ spacing = 16.11. Thermogravimetric analysis indicates z is about 1.53. The packing density ($V_p$) is 1.02 n-pentyl (n=5, z=1.54) Calc.: C, 30.20%; H, 7.20%; N 7.05%. Found: C, 30.19%; H, 7.05%; N 6.58%. X-ray analysis $D_{001}$ spacing = 18.96. Thermogravimetric analysis indicates z is about 1.56. The packing density ($V_p$) is 0.90.

n-hexyl (n=6, z=1.57) Calc.: C, 34.20%; H, 7.73%; N 6.65%. Found: C, 33.76%; H, 7.61%; N 6.66%. X-ray analysis $D_{001}$ spacing = 20.38. Thermogravimetric analysis indicates z is about 1.65. The packing density ($V_p$) is 0.97.

EXAMPLE 3

Intercalation Procedure B

Amines having seven or more carbon atoms are intercalated by refluxing a product of Example 2 in which $C_nH_{2n+1}$ is pentyl (n=5) or hexyl (n=6) with the desired amine (n=7 or more) for 72 hours. Isolation of the product is performed as described in Example 2.

n-octyl (n=8, z=1.81) Calc.: C, 42.85%; H, 8.97%; N 6.25%. Found: C, 42.60%; H, 8.77%; N 6.21%. X-ray analysis $D_{001}$ spacing = 25.09. Thermogravimetric analysis indicates z is about 1.73. The packing density ($V_p$) is 1.09.

n-dodecyl (n=12, z=1.96) Calc.: C, 52.79%; H, 9.90%; N 5.19%. Found: C, 52.70%; H, 10.24%; N 5.06%. X-ray analysis $D_{001}$ spacing = 32.44. Thermogravimetric analysis indicates z is about 1.92. The packing density ($V_p$) is 1.25.

EXAMPLE 4

Intercalation Procedure C

One gram of vanadyl (IV) hydrogen phosphate hemihydrate in a large molar excess of ammonia, methylamine, or ethylamine, is allowed to stand for approximately 15 hours to produce the complexes in which n=0, 1, or 2, respectively.

H (n=0, z=0.86) Calc.: H, 1.38%; N 6.45%. Found: H, 1.71%; N 6.56%. X-ray analysis $D_{001}$ spacing = 6.94. Thermogravimetric analysis indicates z is about 1.14. methyl (n=1) X-ray analysis indicates amorphous material. Thermogravimetric analysis indicates z is about 1.93.

The packing density ($V_p$) is 1.17.

EXAMPLE 5

Calcining Procedure

The complexes obtained in Examples 2–4 are calcined according to the following procedure, exemplified for the complex in which n=3. A total of 1.2 g of the 35–65 mesh fraction of the complex is placed in a reactor (Pyrex glass U-tube) inside an aluminum split block. The reaction vessel is heated at 435° C. for 168 hours while introducing 1.5% n-butane in air at GHSV of 600 h$^{-1}$.

EXAMPLE 6

Oxidation of Butane to Maleic Anhydride

After the activation procedure described in Example 4 was completed, the temperature was lowered to 360°–410° C. and the kinetic data collected. All experiments were carried out in once-through integral mode.

CP grade n-butane and dry air were metered separately using mass flow controllers and mixed in desired proportions.

The effluent stream was analyzed by on-line gas chromatography for molar yields of maleic anhydride, $C_2$ and $C_3$ acids, CO and $CO_2$.

| Catalyst | Temperature | GHSV, $h^{-1}$ | Conversion | Selectivity |
|---|---|---|---|---|
| ammonia | 402° C. | 650 | 28% | 19% |
| propylamine | 401° C. | 700 | 36% | 22% |
| n-butylamine | 402° C. | 750 | 32% | 27% |
| n-hexylamine | 402° C. | 700 | 34% | 44% |
| n-octylamine | 403° C. | 700 | 31% | 50% |

What is claimed is:

1. An intercalated vanadium complex which upon being calcined forms a vanadium/phosphorus oxide oxidation catalyst, said complex having the formula:

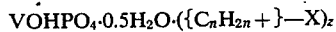

$$VOHPO_4 \cdot 0.5H_2O \cdot (\{C_nH_{2n+}\}-X)_z$$

in which X is an oxygen- or nitrogen-containing functional group operable to form hydrogen bonds with the P—OH and water groups of the complex;

n has a value of from 0 to 20 when X is a nitrogen-containing functional group or a value of from 1 to 20 when X is an oxygen-containing functional group; and z has a value of from about 1.5 to about 1.9.

2. An intercalated vanadium complex according to claim 1 in which X is a primary amino group.

3. An intercalated vanadium complex according to claim 1 in which n has a value of from 1 to 12.

4. An intercalated vanadium complex according to claim 1 in which $C_2H_{2n+1}$ is n-propyl.

5. An intercalated vanadium complex according to claim 1 in which $C_2H_{2n+1}$ is n-butyl.

6. An intercalated vanadium complex according to claim 1 in which $C_2H_{2n+1}$ is n-pentyl.

7. An intercalated vanadium complex according to claim 1 in which $C_2H_{2n+1}$ is n-hexyl.

8. An intercalated vanadium complex according to claim 1 in which $C_2H_{2n+1}$ is n-octyl.

9. An intercalated vanadium complex according to claim 1 in which $C_nH_{2n+1}$ is n-dodecyl.

10. A vanadium/phosphorus oxide oxidation catalyst formed by calcining the intercalated vanadium complex according to claim 1 in the presence of a reducing agent and at a temperature of at least 400° C.

* * * * *